(12) United States Patent
Hatanaka et al.

(10) Patent No.: US 6,211,333 B1
(45) Date of Patent: Apr. 3, 2001

(54) METHOD FOR PRODUCING PEPTIDES AND THEIR SALTS WHICH HAVE AN AGONIST ACTIVITY OF LUTEINIZING HORMONE RELEASING HORMONES SECRETED FROM THE HYPOTHALAMUS

(75) Inventors: Chitoshi Hatanaka, Kyoto; Yasuaki Abe, Hyogo; Mitsuhisa Yamano, Osaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/202,621

(22) PCT Filed: Jun. 19, 1997

(86) PCT No.: PCT/JP97/02097

§ 371 Date: Dec. 18, 1998

§ 102(e) Date: Dec. 18, 1998

(87) PCT Pub. No.: WO97/48726

PCT Pub. Date: Dec. 24, 1997

(30) Foreign Application Priority Data

Jun. 21, 1996 (JP) .................................................. 8-161791

(51) Int. Cl.[7] .............................. C07K 1/02; C07K 1/06; C07K 7/23
(52) U.S. Cl. .............................................. 530/313; 514/15
(58) Field of Search ............................. 530/313; 514/15; 930/130, DIG. 690, DIG. 691, DIG. 692, DIG. 693, DIG. 694, DIG. 695, DIG. 696, DIG. 697, DIG. 698

(56) References Cited

U.S. PATENT DOCUMENTS 3,855,198   12/1974   Sarantakis .......................... 530/313

(List continued on next page.)

FOREIGN PATENT DOCUMENTS 0 033 976   8/1981   (EP) .
0 328 090   8/1989   (EP) .

OTHER PUBLICATIONS

Kobayashi et al. Synthesis of Some Di–and Tri–Substituted Analogs . . . Chem. Pharm. Bull. vol. 23, No. 9, pp. 2033–2038, 1975.*

(List continued on next page.)

Primary Examiner—Jeffrey E. Russel
(74) Attorney, Agent, or Firm—Wenderoth, Lind & Ponack, L.L.P.

(57) ABSTRACT

A peptide of the formula:

$$\text{5-oxo—Pro—}R^1\text{—Trp—Ser—}R^2\text{—}R^3\text{—}R^4\text{—Arg—Pro—}R^6 \quad (I)$$

wherein $R^1$ represents His, Tyr, Trp or p—$NH_2$—Phe, $R^2$ represents Tyr or Phe, $R^3$ represents an optionally substituted Gly or an optionally substituted α-D-amino acid residue, $R^4$ represents Leu, Ile or Nle, $R^6$ represents (1) Gly—NH—$R^7$, wherein $R^7$ represents a hydrogen atom or an alkyl group which may optionally be substituted with a hydroxyl group, or (2) NH—$R^8$, wherein $R^8$ represents a hydrogen atom, an alkyl group which may optionally be substituted with a hydroxyl group or an ureido group (—NH—CO—$NH_2$), is produced advantageously in an industrial scale by reacting a peptide of the formula:

$$\text{5-oxo—Pro—}R^1\text{—Trp—Ser—}R^2\text{—}R^3\text{—OH} \quad (II)$$

wherein $R^1$, $R^2$ and $R^3$ have the same meanings as defined above or its salts, with a peptide of the formula:

$$\text{H—}R^4\text{—}R^5\text{—Pro—}R^6 \quad (III)$$

wherein $R^4$ and $R^6$ have the same meaning as defined above and $R^5$ represents Arg which has been protected or its salts, to produce a peptide of the formula:

$$\text{5-oxo—Pro—}R^1\text{—Trp—Ser—}R^2\text{—}R^3\text{—}R^4\text{—}R^5\text{—Pro—}R^6 \quad (I')$$

wherein $R^1$, $R^2$, $R^3$, $R^4$, $R^5$ and $R^6$ have the same meanings as defined above or its salt, and then subjecting thus obtained peptide (I') to a de-protecting group reaction.

10 Claims, 1 Drawing Sheet

U.S. PATENT DOCUMENTS 3,947,569 * 3/1976 Immer et al. ............................ 436/86
3,997,516   12/1976 Nishimura ............................. 530/316
4,647,553 * 3/1987 Gulyas et al. .......................... 514/15

OTHER PUBLICATIONS

Database WPI, Section Ch, Week 7803, Derwent Publications Ltd., London, GB; Class B04, AN 78–04222a XP002039369 & CA 1 023 350 A, Dec. 17, 1974.

Database WPI, Section Ch, Week 7503, Derwent Publications Ltd., London, GB; Class B04, AN 75–04690w XP002039370 & JP 49 100 081 A, Sep. 1974.

* cited by examiner

Figure 1

METHOD FOR PRODUCING PEPTIDES AND THEIR SALTS WHICH HAVE AN AGONIST ACTIVITY OF LUTEINIZING HORMONE RELEASING HORMONES SECRETED FROM THE HYPOTHALAMUS

BACKGROUND OF THE INVENTION

1. Field of the Invention

This invention relates to a method for producing peptides, which have an activity of an agonist of luteinizing hormone releasing hormones (LHRH) secreted from the hypothalamus or their salts. The present invention further relates to an intermediate peptide, its production method, its crystals and a method for producing the crystals.

2. Description of the Related Art

U.S. Pat. No. 4,008,209 which corresponds to Japanese Patent Application Laid-open No. 50-059370/1975, describes the following method for producing a peptide of the formula: (Pyr)Glu—His—Trp—Ser—Tyr(or Phe)—X—Leu(or Ile, or Nle)—Arg—Pro—NH—R (SEQ ID NO: 13), wherein each amino acid residue has L-configuration unless otherwise indicated; X represents D—Leu, D—NLe, D—NVa, D—Ser, D—Abu, D—Phg, D—Phe or α—Aibu; R represents an alkyl group which may optionally have hydroxyl.

sarily satisfactory at the factory level. Therefore, design of a commercial process for producing a peptide involves many problems that must be solved for satisfying a variety of requirements such as the modality of peptide chain extension; the selection of the site of fragment condensation; the method for inhibiting isomerization at condensation of fragments; the selection of protective groups for the α-position and side-chain functional groups; the method for final elimination of such protective groups; the method for purification of the end product peptide; and the overall operability of the series of steps, among others.

Furthermore, a diversity of methods and a variety of reaction conditions may be contemplated for the synthesis of peptides in general but it is often the case that because of non-crystallizability, many intermediates used in the process cannot be sufficiently purified or require time-consuming fractionation procedures, with the result that many processes are not satisfactory in the reproducibility of quality and yield. Thus, the physical characteristics such as crystallizability, stability, and solubility of intermediates, which are key factors in the respective production stages, hold sway over whether a process can be commercially acceptable in many cases.

Referring to the methodology for production of the peptide of the formula:(Pyr)Glu—His—Trp—Ser—Tyr(or Phe)—X—Leu(or Ile, or Nle)—Arg—Pro—NH—R (SEQ ID NO: 13), the process disclosed in U.S. Pat. No. 4,008, In the reaction scheme, all symbols have the same meanings as defined above.

Japanese Patent Application Laid-open No. 51-6926/1996, which corresponds to U.S. Pat. No. 3,997,516, describes a method for producing a peptide having a guanidino group which comprises protecting the guanidino group of a guanidino group-containing peptide with a lower alkoxybenzenesulfonyl group or tri(lower)alkylbenzenesulfonyl group.

Furthermore, Japanese Patent Application Laid-open No. 51-100030/1996, which corresponds to U.S. Pat. No. 3,997,516, describes a method for producing a peptide having a guanidino group which comprises protecting the guanidino group of a guanidino group-containing peptide with a lower alkoxybenzenesulfonyl group or tri(lower)alkylbenzenesulfonyl group and, after the peptide condensation reaction, removing the protective group with a halogenosulfonic or lower alkylsulfonic acid or a Lewis acid.

For the production of a peptide on a commercial scale, it is essential that various parameters such as (1) qualities of starting materials, (2) production cost, (3) workability, (4) safety to operators, and (5) prevention of pollution should satisfy certain practically acceptable levels and every process that is satisfactory at the laboratory level is not neces- 209, which corresponds to Japanese Patent Application Laid-open No. 50-059370/1975, protects the guanidino group of Arg with nitro and, therefore, the group Z used for protecting the α-amino group can hardly be reductively eliminated selectively, so that HBr—AcOH is used for removal of group Z. Inevitably, in this process, benzyl bromide, which is highly lacrimetory, is by-produced in a large quantity and, moreover, a large amount of ether must be used for isolation of the end product. In addition, while the end product of this reaction is usually recovered in the hydrobromide form, the hydrogen bromide must be removed with, for example, an ion exchange resin in order that the objectionable isomerization on condensation of fragments may be inhibited. Furthermore, while the gradient elution method is used in the chromatographic purification of the final end product, the above peptide, the lower reproducibility of the concentration gradient necessitates rigorous qualitative testing, with the result that the operation for steady production of the desired product of uniform quality cannot be stand-ardized. Therefore, the process is not suited for industrial-scale production.

Furthermore, in the U.S. Pat. No. 3,997,516, a reaction scheme produces a peptide of the formula: (Pyr)Glu—His—Trp—Ser—Tyr—D—Leu—Leu—Arg(MBS)—Pro—

NH—C$_2$H$_5$ (SEQ ID NO: 14) wherein MBS denotes p-methoxybenzenesulfonyl group. However, in the U.S. patent, only the reaction scheme is described, but other details such as reaction conditions are not described at all.

Thus, an industrially profitable process for producing peptides which have an activity of an agonist of LHRH or its salts with safety, expedience, high yield and good reproducibility has not yet been developed.

The inventors of the present invention explored the above-mentioned problems with diligence and succeeded in establishing a protocol for the effective production of intermediate peptide (II), mentioned below, through inhibition of isomerization of amino acid residues in the hydrolysis reaction step, a protocol for crystallization of the peptide (II); and deprotection on an industrial scale of peptide (I'), mentioned below; and a protocol for industrial-scale purification of the objective peptide (I), mentioned below. Accordingly, the inventors arrived at a process for producing said peptide (I) with safety, high yield, and good reproducibility, and have completed the present invention.

SUMMARY OF THE INVENTION

The present invention is directed to (1) A method for producing a peptide of the formula:

5—oxo—Pro—R$^1$—Trp—Ser—R$^2$—R$^3$—R$^4$—Arg—Pro—R$^6$   (I) (SEQ ID NO: 6)

wherein R$^1$ represents His, Tyr, Trp or p—NH$_2$—Phe, R$^2$ represents Tyr or Phe, R$^3$ represents an optionally substituted Gly or an optionally substituted α-D-amino acid residue, R$^4$ represents Leu, Ile or Nle, R$^6$ represents (1) Gly—NH—R$^7$, wherein R$^7$ represents a hydrogen atom or an alkyl group which may optionally be substituted with a hydroxyl group or (2) NH—R$^8$, wherein R$^8$ represents a hydrogen atom, an alkyl group which may optionally be substituted with a hydroxyl group or an ureido group (—NH—CO—NH$_2$), or its salts, which comprises reacting a peptide of the formula:

5—oxo—Pro—R$^1$—Trp—Ser—R$^2$—R$^3$—OH (II) (SEQ ID NO: 4)

wherein R$^1$, R$^2$ and R$^3$ have the same meanings as defined above or its salts, with a peptide of the formula:

H—R$^4$—R$^5$—Pro—R$^6$   (III) (SEQ ID NO: 15)

wherein R$^4$ and R$^6$ have the same meaning as defined above and R$^5$ represents Arg which has been protected, or its salts, to produce a peptide of the formula:

5—oxo—Pro—R$^1$—Trp—Ser—R$^2$—R$^3$—R$^4$—R$^5$—Pro—R$^6$   (I') (SEQ ID NO: 5)

wherein R$^1$, R$^2$, R$^3$, R$^4$, R$^5$ and R$^6$ have the same meanings as defined above, or its salt, and then subjecting thus obtained peptide (I') to a de-protecting group reaction, (2) A method according to the item (1), wherein R$^1$ is His, R$^2$ is Tyr, R$^3$ is Gly, D—Leu, D—Trp, D—Val which may be substituted with C$_{1-4}$ alkyl, D—Ser, D—Ala which may be substituted with C$_{1-4}$ alkoxy, with naphthyl or with 2-methylindolyl, or D—His which may be substituted with C$_{7-10}$ aralkyl, R$^4$ is Leu, R$^5$ is Arg which is protected with a group selected from the group consisting of a C$_{1-6}$ alkoxybenzenesulfonyl group, tri—C$_{1-6}$ alkylbenzenesulfonyl group and a nitro group, R$^6$ is a group of the formula: NH—R$^{8'}$, wherein R$^{8'}$ is a hydrogen atom or an alkyl group which may optionally be substituted with hydroxyl, (3) A method according to the item (1), wherein R$^1$ is His, R$^2$ is Tyr, R$^3$ is D—Leu, R$^4$ is Leu, R$^5$ is Arg which is protected with a C$_{1-6}$ alkoxybenzenesulfonyl group, R$^6$ is a group of the formula: NH—R$^{8''}$, wherein R$^{8''}$ is a C$_{1-3}$ alkyl group which may optionally be substituted with hydroxyl, (4) A method according to the item (1), wherein the reaction of the peptide (II) or its salts with the peptide (III) or its salts is carried out at a temperature ranging from about 0 to 40° C. for about 30 to 60 hours,

(5) A method according to the item (1), wherein an acid is used in the de-protecting group reaction, (6) A method according to the item (5), wherein the acid is C$_{1-6}$ alkylsulfonic acid, (7) A method according to the item (5), wherein the acid is used at a ratio of about 5 to 25 times (weight) of the peptide (I'), (8) A method for recovering and purifying the peptide (I) as defined in the above item 1, which comprises subjecting the reaction mixture containing an emerged oily product of a free form to a purification of column chromatography, the reaction mixture being obtained by the reaction of de-protecting group reaction of the Peptide (I') under the existence of an acid and then neutralized with a base, (9) A peptide of the formula:

5—oxo—Pro—R$^1$—Trp—Ser—R$^2$—R$^3$—OR(IV) (SEQ ID NO: 3)

wherein R$^1$ is His, Tyr, Trp or p—NH$_2$—Phe, R$^2$ is Tyr or Phe, R$^3$ is optionally substituted Gly or an optionally substituted α-D-amino acid residue and R$^9$ is a protecting group, or its salt, (10) A peptide according to the item (9), wherein R$^1$ is His, R$^2$ is Tyr, R$^3$ is Gly, D—Leu, D—Trp, D—Val which may be substituted with C$_{1-4}$ alkyl, D—Ser, D—Ala which may be substituted with C$_{1-4}$ alkoxy, with naphthyl or with 2-methylindolyl, or D—His which may be substituted with C$_{7-10}$ aralkyl, R$^9$ is C$_{1-6}$ alkyl, C$_{6-10}$ aryl or C$_{7-12}$ aralkyl, or its salt, (11) A peptide according to the item (9), wherein R$^1$ is His, R$^2$ is Tyr, R$^3$ is D—Leu, R is C$_{1-6}$ alkyl, or its salt, (12) A method for producing a peptide of the formula:

5—oxo—Pro—R$^1$—Trp—Ser—R$^2$—R$^3$—OH (II) (SEQ ID NO: 4)

wherein R$^1$ is His, Tyr, Trp or p—NH$_2$—Phe, R$^2$ is Tyr or Phe, R$^3$ is optionally substituted Gly or an optionally substituted α-D-amino acid residue, or its salt, which comprises hydrolyzing a peptide of the formula:

5—oxo—Pro—R$^1$—Trp—Ser—R$^2$—R$^3$—OR(IV) (SEQ ID NO: 3)

wherein R$^1$, R$^2$ and R$^3$ have the same meanings as defined above, R$^9$ is a protecting group, or its salt, (13) A crystal of a peptide of the formula:

5—oxo—Pro—R$^1$—Trp—Ser—R$^2$—R$^3$—OH (II) (SEQ ID NO: 4)

wherein R$^1$ is His, Tyr, Trp or p—NH$_2$—Phe, R$^2$ is Tyr or Phe, R$^3$ is optionally substituted Gly or an optionally substituted α-D-amino acid residue, or its salt, (14) A method for producing a crystal of a peptide of the formula:

5—oxo—Pro—R$^1$—Trp—Ser—R$^2$—R$^3$—OH (II) (SEQ ID NO:4)

wherein R$^1$ is His, Tyr, Trp or p—NH$_2$—Phe, R$^2$ is Tyr or Phe, R$^3$ is optionally substituted Gly or an optionally substituted α-D-amino acid residue, or its salt, which comprises subjecting a solution of the peptide (II) or its salt to aging, and (15) A method according to the item (14), wherein the solution of the peptide (II) or its salt with the concentration of about 0.01 to 0.05 mole/liter is subjected to aging at a temperature ranging from about 10 to 70° C. for about 10 to 70 hours.

DESCRIPTION OF THE PREFERRED EMBODIMENTS

The meanings of the symbols and/or abbreviations are shown below:

$R^1$ denotes His, Tyr, Trp or p—$NH_2$—Phe, and His is preferable.

$R^2$ denotes Tyr or Phe, and Tyr is preferable.

As α-D-amino acid residue in the optionally substituted α-D-amino acid residue, mention is made of D—Leu, D—Ile, D—Nle, D—Val, D—Nva, D—Ser, D—Abu, D—Phe, D—Phg, D—Thr, D—Met, D—Ala, D—Trp or α-Aibu. As the α-D-amino acid residue, D—Leu, D—Val, D—Ser, D—Trp, D—Ala, D—Abu and α-Aibu are preferable, and D—Leu is more preferable.

As the substituent on the Gly or α-D-amino acid residue, mention is made of (1) mono-$C_{1-4}$ alkyl, e.g. methyl, ethyl, n-propyl, isopropyl, n-butyl, t-butyl, (2) di $C_{1-4}$ alkyl, e.g. dimethyl, diethyl, (3) tri $C_{1-4}$ alkyl, e.g. trimethyl, triethyl, (4) $C_{1-4}$ alkoxy, e.g. methoxy, ethoxy, n-propoxy, isopropoxy, n-butoxy, t-butoxy, (5) $C_{6-10}$ aryl, e.g. phenyl, naphthyl, (6) $C_{7-10}$ aralkyl, e.g. benzyl, phenethyl, (7) indolyl, (8) methylindolyl and (9) benzylimidazolyl. Among others, methyl, dimethyl, trimethyl, t-butyl, t-butoxy, 2-naphtyl, indol-3-yl, 2-methylindolyl and benzylimidazol-2-yl. Especially, trimethyl, t-butyl, t-butoxy, 2-naphthyl, indol-3-yl, 2-methylindolyl and benzylimidazol-2-yl are more preferable.

As preferable example of $R^3$, mention is made of Gly, D—Leu, D—Trp, D—Val which may be substituted with $C_{1-4}$ alkyl, D—Ser, D—Ala which may be substituted with $C_{1-4}$ alkoxy, with naphthyl or with 2-methylindolyl, or D—His which may be substituted with $C_{7-10}$ aralkyl.

As more preferable examples of $R^3$, mention is made of Gly, D—Leu, D—Trp, 3-methyl-D—Val, D—Ser, t-butoxy-D—Ala, 2-naphthyl-D—Ala, 2-methylinolyl-D—Ala, benzylimidazol-2-yl—D—Ala (=$N^{im}$-benzyl-D—His).

$R^4$ denotes Leu, Ile or Nle. As $R^4$, Leu is preferable.

As the protecting group in the protected Arg of $R^5$, mention is made of an alkoxybenzenesulfonyl group, a trialkylbenzenesulfonyl group.

The alkoxybenzenesulfonyl is preferably a $C_{1-6}$ alkoxy-substituted benzenesulfonyl group such as p-methoxybenzenesulfonyl, p-ethoxybenzenesulfonyl, p-isopropoxybenzenesulfonyl, etc. and more preferably is p-methoxybenzenesulfonyl.

The alkyl moieties in the trialkylbenzenesulfonyl group are preferably $C_{1-6}$ alkyl groups, same or different, such as methyl, ethyl, propyl, n-butyl, t-butyl, n-pentyl, t-pentyl, etc. The three alkyl groups may be present in optional substitutable positions on the benzene ring of benzenesulfonyl but are preferably situated in the 2-, 4-, and 6-positions with respect to the sulfonyl group. Specifically, 2,4,6-trimethylbenzenesulfonyl, 2,4,6-triethylbenzenesulfonyl, 2,4,6-tripropylbenzenesulfonyl, 2,4,6-triisopropylbenzenesulfonyl, 2,4,6-tri—t-butylbenzenesulfonyl, etc. can be typically mentioned.

As more preferable examples of the protecting group in the protected Arg of $R^5$, mention is made of $C_{1-6}$ alkoxy-benzenesulfonyl group, more preferably p-methoxybenzenesulfonyl, p-ethoxybenzenesulfonyl, p-propoxybenzenesulfonyl, p-isopropoxybenzenesulfonyl, still more preferably p-methoxybenenesulfonyl.

The alkyl group of the "alkyl which may optionally have hydroxyl" mentioned for the group $R^7$ and $R^8$ is a $C_{1-4}$ alkyl group such as methyl, ethyl, n-propyl, isopropyl, n-butyl, isobutyl, sec-butyl or tert-butyl, and is preferably ethyl, which may have hydroxyl in any substitutable position.

As preferable example of the alkyl which may optionally have hydroxyl, mention is made of hydroxymethyl, 2-hydroxyethyl, 3-hydroxy-n-propyl, 4-hydroxy-n-butyl, etc, and 2-hydroxyethyl is still more preferable.

As the protecting group of $R^9$, mention is made of $C_{1-6}$ alkyl, e.g. methyl, ethyl, n-propyl, isopropyl, n-butyl, isobutyl, t-butyl, n-pentyl, n-hexyl, etc, $C_{7-10}$ aralkyl, e.g. benzyl, phenethyl, etc. The group $R^9$ is preferably $C_{1-3}$ alkyl, more preferably ethyl.

Throughout this specification (and appended claims), amino acids and peptides are referred to by the abbreviations according to IUPAC-IUB Commission on Biological Nomenclature or by the trivial names which are in routine use in the art. Where any amino acid may exist as optical isomers, the L-compound is meant unless otherwise indicated.

It should also be understood that the following abbreviations, among others, are sometimes used in this specification.

Gly : glycine
Ala alanine
Val : valine
Leu leucine
Ile isoleucine
Ser serine
Thr : threonine
Arg : arginine
Phe : phenylalanine
Tyr : tyrosine
His : histidine
Trp : tryptophan
Pro : proline
NLe : norleucine
NVa : norvaline
Abu : 2-aminobutyric acid
Phg : phenylglycine
α-Aibu: α-aminoisobutyric acid
P—$NH_2$—Phe: p-aminophenylalanine
Z : benzyloxycarbonyl
Pd : palladium
Pd—C : palladium-carbon
Et : ethyl
AcOH : acetic acid
HF : hydrogen fluoride
HBr : hydrogen bromide
DCHA : dicyclohexylamine
DMF : N,N-dimethylformamide
DMA : N,N-dimethylacetamide THF : tetrahydrofuran
MSA : methanesulfonic acid
MBS : p-methoxybenzenesulfonyl
DCC : N,N'-dicyclohexylcarbodiimide
HONB : N-hydroxy-5-norbornene-2,3-dicarboximide
HOSu : N-hydroxysuccinimide
HOBt : 1-hydroxybenzotriazole
EDA : ethyl-3-(3-dimethylamino)propylcarbodiimide hydrochloride
NP : p-nitrophenyl
HPLC : High performance liquid chromatography Methods for the production of the peptide (I) are described below:

A variety of synthetic routes can be contemplated for the production of the peptide of the formula (I) or its salt and a diversity of combinations are available in regard to amino- and carboxy-protecting groups, methods for amide bond formation, methods for deprotection, and methods for purification of peptides obtained in the respective routes of synthesis.

Figure 1:
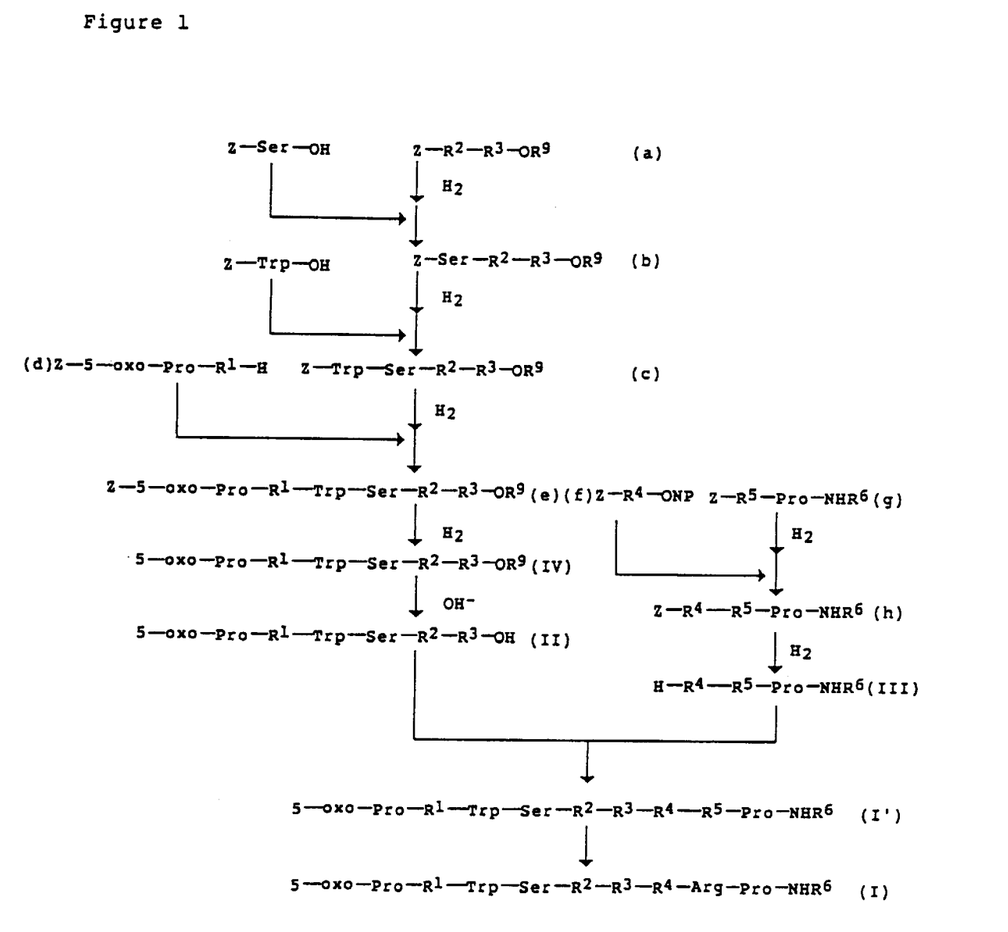
FIG. 1 is a typical flow chart showing a preferred process of the present invention.

Among such alternatives the synthetic route of FIG. 1 is one of preferred examples. Thus, the production technology of the present invention comprises (1) protecting the guanidino group of $Arg^8$ with a protecting group, (2) synthesizing two key intermediate fragments, e.g. Peptide (II) and Peptide (III), and (3) de-protecting the precursor peptide (I'), which is available upon condensation of said peptides from the guanidino group of $Arg^8$ to provide the objective peptide (I) or salt thereof.

As the salt of the present peptide, mention is made of salts with an organic acid, e.g. formic acid, acetic acid, propionic acid, lactic acid, glucollic acid, pyroracemic acid, oxalic acid, malonic acid, succinic acid, maleic acid, fumaric acid, p-toluenesulfonic acid, trifluoroacetic acid, methanesulfonic acid, phosphoric acid, etc, an inorganic acid, e.g. hydrochloric acid, hydrobromic acid, sulfuric acid, etc.

1. Method for producing Peptide (a)

The peptide of the formula (a), whose structure being shown as $Z-R^2-R^3-OR^9$, can be produced by a manner described in "Peptide Gousei-no-Kiso-to-Jikken" (Basis and Experiment of Peptide Synthesis), edited by Nobuo Izumiya et al., Maruzen Publishers, Japan; or "The Peptide", vol. 1, pages 76–136, Ebehard Schroder and Klaus Lubke, or in a similar manner thereto.

2. Method for producing Peptide (b) from Peptide (a)

In the production process of the present invention, peptide (b), $Z-Ser-R^2-R^3-OR^9$ which is shown in FIG. 1, is synthesized by condensing the dipeptide (a) with Z-Ser.

At first, the peptide (a) is subjected to a reaction of elimination of the group Z to produce de—Z peptide (a) (peptide (a) minutes "Z" group). As the elimination reaction, catalytic reduction using a catalyst such as Pd, Pd—C, and HBr/AcOH treatment are preferable.

As the solvent in the catalytic reduction, alcohols, e.g. methanol, ethanol, isopropanol, n-propanol, n-butanol, t-butanol, etc, ethers, such as THF, dioxane, etc amides, such as DMF, DMA, etc, are mentioned. Among others, DMF, DMA or THF is used advantageously, because concentration is unnecessary in pre-stage of the next reaction step. The reaction temperature is about 0 to 50° C., preferably about 20 to 40° C. The reaction time is about 3 to 15 hours, preferably about 5 to 10 hours. This reaction is preferably conducted under a normal pressure.

Alternatively, in order to decrease the occurrence of di-ketopiperazine at the reduction reaction, it is preferable to subject de—Z peptide (a) to a protonation reaction before the catalytic reduction. At the protonation reaction, an acid is added to the reaction system. As the acid, mention is made of inorganic acid or organic acid, preferably hydrochloric acid, sulfuric acid, p-toluenesulfonic acid. Among them, p-toluenesulfonic acid is more preferable. The amount of the acid is preferably about 0.8 to 1.5 times (mole/mole), more preferably 1 to 1.1 times (mole/mole), that of de—Z peptide (a).

The HBr/AcOH treatment is carried out by reacting Peptide (a) with HBr together with a saturated acetic acid without any solvent. The reaction temperature is about −10 to 30° C., preferably about 10 to 20° C. The reaction time is about 10 minutes to 2 hours, preferably about 30 minutes to one hour. The recovery of the objective peptide from the reaction mixture is carried out by recovering the emerged precipitate by adding ether, ethyl acetate and so on, and then by drying.

In the reaction of the introduction of Z—Ser group, the active ester method is used, i.e. converting the peptide to an active ester, and, the intramolecular dehydration reaction is successfully inhibited by optimization of reaction temperature. The active ester that can be used for the introduction of Z—Ser in the process of the invention includes various active esters that can be used in peptide synthesis, such as the esters with an active esterification agent, e.g. N-hydroxy-5-norbornene-2,3-dicarboximide (HONB), N-hydroxysuccinimide (HOSu), N-hydroxybenzotriazole (HOBt), etc. Particularly preferred is the HONB ester.

For preparing an active ester of Z—Ser—OH, Z—Ser—OH is reacted with an active esterification agent in a solvent such as ethers, e.g. diethylether, isopropylether, THF, dioxane, etc, amides, e.g. DMF, DMA, etc, acetonitrile, acid esters, e.g. methyl formate, methyl acetate, ethyl acetate, etc, at a temperature ranging from about −5 to 20° C., preferably about 0 to 5° C., for about 5 to 15 hours, preferably about 7 to 10 hours;

The reaction of de—Z peptide (a) an active ester of and Z—Ser—OH is carried out in an inert solvent. The solvent used in the reduction reaction in the former step may be used. Among others, amides, e.g. DMF, DMA, are preferable. The reaction is carried out at a lower temperature such as a temperature ranging from −10 to 10° C., preferably about −5 to 5° C., for about 5 to 20 hours, preferably about 7 to 12 hours.

3. Method for producing Peptide (c) from Peptide (b)

Peptide (c), $Z-Trp-Ser-R^2-R^3-OR^9$ (SEQ ID NO: 1) which is shown in FIG. 1, is produced by subjecting a peptide obtained by de—Z reaction of Peptide (b) (de—Z peptide (b)) with a peptide, Z—Trp—OH to a condensation reaction.

The de—Z reaction is carried out by a catalytic reduction by employing a catalyst such as Pd, Pd—C, or by a treatment using HBr/AcOH treatment. The catalytic reduction and HBr/AcOH treatment is carried out by a manner similar to those mentioned in the method for producing Peptide (b) from Peptide (a).

Introduction of Z—Trp into the peptide obtained by de—Z reaction of Peptide (b) can be carried out by reacting Peptide (b) with an active ester of Z—Trp—OH, which is previously produced by reacting Z—Trp—OH with an active esterification agent, e.g. HONB, HOBt, HOSu, in the presence of a condensation agent, e.g. DCC, EDA, etc. Also, Peptide (b) and Z—Trp—OH can be condensed by reacting both using a condensation agent in the presence of an active ester.

As the active ester, HONB is preferable, and as the condensation agent, DCC is preferable. The method for producing active ester of Z—Trp—OH can be a similar manner as above.

The reaction of Peptide (b) with the active ester of Z—Trp—OH in the presence of a condensation agent is carried out at a temperature ranging from about 0 to 20° C., preferably about 5 to 10° C. for about 5 to 20 hours, preferable about 7 to 10 hours.

4. Method for producing Peptide (e) from Peptide (c) and Peptide (d)

Peptide (d), Z-5-oxo—Pro—$R^1$—OH, can be produced by the method of Hatanaka et al. [Takeda Research Report, 35, 16 (1976); Biochemical and Biophysical Research Communications, 60, 1345 (1974)], or a similar method as above.

Peptide (e), Z-5-oxo—Pro—$R^1$—Trp—Ser—$R^2$—$R^3$—$OR^9$ (SEQ ID NO:2), is produced by a condensation reaction of Peptide (c) with Peptide (d). In the condensation, attention must be paid to the isomerization of the His residue but any of the known anti-isomerizing procedures available for the fragment condensation of peptides can be utilized. A typical procedure for suppressing this isomerization consists in the use of an anti-isomerizing agent in addition to a condensing agent. The condensing agent may for example be DCC or EDA and the anti-isomerizing agent may for example be HONB, HOSu, HOBt, (HOSu), or the like. These two kinds of agents can be used in any desired combination. Typical combinations are DCC—HONB, DCC—HOSu, DCC—HOBt, and EDA—HOSu, among others. Particularly preferred is DCC—HONB. While the reaction temperature is a major factor in the control of isomerization, the preferred reaction temperature is about 0 to 20° C., preferably about 5. to 15° C. for 30 minutes to 100 hours, preferably about 50 to 80 hours. In the reaction, as a solvent, use is made of amides, e.g. DMF, DMA, etc, ethers, e.g. 2-methylpyrrolidone, THF, dioxane, etc.

5. Method for producing Peptide (IV) from Peptide (e)

Elimination of Z from Peptide (e), Z-5-oxo—Pro—$R^1$—Trp—Ser—$R^2$—$R^3$—$OR^9$ (SEQ ID NO: 2), gives Peptide (IV). The de—Z reaction is carried out with methods such as catalytic reduction with a catalyst, e.g. Pd, Pd—C, or the like, or HBr/AcOH treatment.

In the catalytic reduction, as a solvent, use is made of amides, e.g. DMF, DMA, etc, ethers, e.g. 2-methylpyrrolidone, THF, dioxane, etc, or t-butanol, at a temperature ranging from about 0 to 50° C., preferably about 25 to 40° C., for about 1 to 10 hours, preferably about 3 to 6 hours.

The HBr/AcOH treatment is carried by a method similar to those mentioned in the reaction from Peptide (a) to Peptide (b).

6. Method for producing Peptide (II) from Peptide (IV)

Peptide (II) can be produced by hydrolyzing Peptide (IV), and if necessary, neutralizing the reaction mixture.

This hydrolysis reaction is preferably carried out in a mixture of water and an alcohol at a low temperature. The alcohol that can be used includes methanol, ethanol, propanol, n-butanol, etc. and the proportion of the alcohol in the water-alcohol mixture is about 1 to 30% (v/v), preferably about 1 to 10% (v/v). The larger the proportion of the alcohol, the lower is the velocity of hydrolysis reaction and, at the same time, the rates of isomerization of $His^2$ and $Ser^4$ are significantly increased (when $R^1$ is His). These isomers cannot be efficiently removed even by the column chromatographic system used in purification, thus detracting from the quality of the final product, Peptide (I).

The reaction solvent may contain the solvent carried over from the upstream stage, viz. DMF, THF, or the like, but its proportion should not be large enough to retard the reaction in any appreciable measure, i.e. preferably about 1 to 20% (v/v), preferably about 5 to 10% (v/v).

The hydrolysis is carried out in the presence of alkali. As the alkali, mention is made of sodium hydroxide, potassium hydroxide, calcium hydroxide, barium hydroxide. The reaction speed of hydrolysis and isomerization of His at 2-position and Ser at 4-position depend upon the amount of alkali and its concentration in the solution. The amount of the alkali is preferably about 2.5 to 2 times mole/mole per Peptide (IV), preferably about 3 to 4 times mole/mole. In particular, the concentration of alkali in the reaction system at the initial time of the reaction is preferably about 0.05 to 0.3 mole/liter, more preferably about 0.1 to 0.2 mole/liter. The reaction temperature should be maintained at about −10 to 10° C., preferably about −5 to 5° C., up till completion of the after-treatment, namely neutralization. In order to keep the reaction temperature constant, the reaction system is preferably agitated. This reaction generally goes to completion in 1.5 to 3 hours. In order that the objectionable isomerization may be minimized, the neutralization procedure is preferably carried out immediately following the reaction. This neutralization is carried out at a temperature ranging from −5 to 5° C., preferably −2 to 2° C. using an acid (e.g. hydrochloric acid, sulfuric acid, etc.).

The peptide (II) can be crystallized by the following method:

Thus, the gels formed in the neutralization of the reaction mixture following hydrolysis of (IV) are dissolved by heating and then allowed to cool gradually to let Peptide (II) crystallize out. The dissolution by heating is carried out at a temperature ranging from about 60 to 80° C., preferably about 65 to 75° C. under stirring. This crystallization can be faciliated by adding seed crystals in the cooling phase. As to the timing of addition, seed crystals can be added at any time during the phase where the added seed crystals will not dissolve in the solution and the hot solution will not give rise to gels again. Preferred is the phase where the temperature of the solution is about 35 to 45° C. The gradual cooling is carried out for about 1 to 3 hours, at a temperature ranging from 15 to 30° C.

In order to complete the crystallization, it is preferable to subject the product to aging. The time for aging for obtaining crystals of Peptide (II), which have excellent properties with a high yield, is about 30 to 150 hours, preferably about 60 to 100 hours. The temperature of aging is preferably about 10 to 35° C., more preferably about 10 to 30° C., still more preferably about 15 to 25° C.

As the concentration of Peptide (II) in the solution at the initial time of aging, about 0.01 to 0.05 mole/liter is provided, preferably about 0.02 to 0.04 mole/liter.

In the course of aging, it is preferable to stir the Peptide (II)-containing solution intermittently, for shortening the aging time and/or obtaining a high yield of the crystals. Thus it is preferable to stir the solution for about one minute at about 30 to 35 rpm commencing five hours into the reaction. Thereafter, the solution is stirred for about one minute at about 30 to 35 rpm about every five hours until the aging process is ⅔ completed. Thereafter, the solution is stirred for about one minute at about 30 to 35 rpm about every 0.5 hours until the final step of aging.

More concretely, e.g., the aging time is 60 hours, the solution is stirred at 33 rpm for 1 minute every 5 hours beginning 5 hours into the reaction, until 40 hours. Thereafter, the solution is stirred at 33 rpm for 1 minute every 0.5 hour from 40 hours after the starting of the aging to the last step.

By the above crystallization procedure for Peptide (II), the time-consuming operations for removal of contaminants that would affect the final product quality, such as the His isomer by-produced in the fragment condensation reaction of Peptide (c) to Peptide (e) and hydrolysis reaction of Peptide (IV) to Peptide (II) and the Ser isomer by-produced in the hydrolysis reaction of Peptide (IV) to Peptide (II), as well as the procedure for isolation of Peptide (IV), can all be omitted.

The Peptide (II) can be used for the next reaction in the form of a salt with an alkali metal, e.g. Li, Na, K, Ca, Ba, etc., or an organic base, e.g. triethylamine, cyclohexylamine, dicyclohexylamine, either as isolated by a known method such as crystallization or in the solution form as such.

7. Production of Peptide (III)

Peptide (III) or a salt thereof can be produced by the method of Fujino et al. Archives of Biochemistry and Biophysics, 154, 488 (1973); Chemical and Pharmaceutical Bulletin, 23, 229 (1975)] or any other known method for peptide synthesis.

Peptide (III) can be used for the next reaction in the form of a salt with, for example, hydrochloric acid, hydrobromic acid, sulfuric acid, p-toluenesulfonic acid, trifluoroacetic acid, or methanesulfonic acid, either as isolated by a known separation procedure such as crystallization or in the solution form as such. In such cases, however, the amide bond-forming reaction has to be preceded by elimination of the base (acid) by neutralization with a base or treatment with an ion exchange resin.

8. Production of Peptide (I') from Peptide (II) and Peptide (III)

The condensation reaction of Peptide (II) with Peptide (III) to give Peptide (I') is carried out in a solvent which does not interfere with the reaction. The solvent that can be used includes N,N-dimethylformamide (DMF), N,N-dimethylacetamide (DMA), N-methylpyrrolidone, dichloromethane, dichloroethane, tetrahydofuran, dioxane, etc. and these solvents can be used as a suitable mixture. Preferred are N,N-dimethylformamide and N,N-dimethylacetamide.

The proportion of Peptide (III) relative to Peptide (II) is about 0.5 to 2 molar equivalents, preferably about 1 to 1.5 molar equivalents.

The reaction temperature is generally about 0 to 40° C. and preferably about 5 to 25° C. The range of the temperature is important for preventing isomerization of $R^3$. The reaction time is generally about 30 to 60 hours and preferably about 40 to 50 hors.

In the condensation reaction of Peptide (c) with Peptide (d), attention must be paid to the isomerization of the group $R^3$ but any of the known anti-isomerizing procedures available for the fragment condensation of peptides can be utilized. A typical procedure for suppressing this isomerization (racemization) consists of the use of an anti-isomerizing agent in addition to a condensing agent. The condensing agent may for example be DCC or EDA and the anti-isomerizing agent may for example be HONB, HOSu, HOBt, or the like. These two kinds of agents can be used in any desired combination. Typical combinations are DCC—HONB, DCC—HOSu, DCC—HOBt, and EDA—HOSu, among others. Particularly preferred is DCC—HONB.

The condensing agent is used at a ratio of one to 3 times (mole/mole) of Peptide (II), preferably one to two times (mole/mole). The amount of anti-isomerizing agent is one to 4 times (mole/mole) of Peptide (II), preferably 1.5 to 2.5 times (mole/mole). The initial concentration of Peptide (II) is about 0.05 to 0.2 mole/liter, preferably 0.08 to 1.5 mole/liter. Peptide (III) is used in an amount of 0.8 to 2 times (mole/mole), preferably 1 to 1.3 times (mole/mole), relative to Peptide (II).

9. Production of peptide (I) from Peptide (I')

The deprotection reaction for removing the protective group from the Arg residue of Peptide (I') to give Peptide (I) can be carried out with an acid in a solvent that does not interfere with the reaction or in the absence of a solvent. The solvent that does not interfere with this deprotection reaction includes but is not limited to dichloromethane, dichloroethane, dioxane, and trifluoroacetic acid, and these solvents can be used as a suitable mixture.

The acid that can be used for this deprotection reaction includes but is not limited to $C_{1-6}$ alkanesulfonic acids, e.g. methanesulfonic acid, ethanesulfonic acid, etc., halogenosulfonic acids, e.g. chlorosulfonic acid, fluorosulfonic acid, bromosulfonic acid, etc, and Lewis acids, e.g. boron tris (trifluoroacetate), etc. Among these, $C_{1-3}$ alkanesulfonic acids are preferred and methanesulfonic acid is particularly preferred.

The proportion of the acid for use in this deprotection procedure is about 5 to 25 (w/w) times, preferably about 10 to 20 (w/w) times, based on the weight of Peptide (I').

The deprotection reaction temperature is generally about 0 to 20° C. and preferably about 5 to 15° C.

The deprotection reaction time is generally about 2 to 8 hours and preferably about 4 to 6 hours.

This deprotection reaction is preferably carried out using methanesulfonic acid in the absence of a solvent.

In conducting this deprotection reaction, a radical scavenger (e.g. phenol, anisole, etc.) and/or an antioxidant (e.g. thioglycolic acid) may be added each in a suitable amount. Their amount may each be about 0.8 to 2 (w/w) times, preferably about 0.05 to 2 (w/w) times, based on the above-mentioned reaction product.

When the deprotection reaction is conducted using a $C_{1-6}$ alkanesulfonic acid, the alkanesulfonic acid can be eliminated from the reaction mixture by, for example, the method comprising washing the reaction mixture with ether, dissolving water in the washes, and running the resulting solution on an anion exchange resin column. However, when this method is applied to commercial-scale production, the risk of using a large quantity of ether because the solubility of $C_{1-6}$ alkylsulfonic acid in ether is very low, the risk of abrupt evolution of heat at the mixing of a large quantity of the alkanesulfonic acid with water and upon running the solution on the ion exchange resin column, and the decomposition of the objective peptide due to the evolved heat make the method unsuitable from the standpoints of hardware required, workability, and safety.

As a commercially advantageous method free of the above problems, there is a technology for eliminating the alkanesulfonic acid from the reaction mixture by direct neutralization with a basic aqueous medium. However, in this neutralization process involving neutralization of a large quantity of the strong acid, evolution of an intense heat of neutralization is naturally expected despite the advantage of feasibility of large-scale treatment. In addition to the problem that a large quantity of the neutralized solution must be handled, the adverse influences on the quality of the end product compound due to cleavage of peptide bonds and isomerization of amino acid residues of the objective peptide in the basic aqueous medium are inevitable so that the method was considered to be lacking in common sense as far as the production of peptides is concerned.

However, the inventors of the present invention explored into the methodology for absorbing the heat of neutralization evolved in this neutralization reaction as well as the procedural aspect of the methodology and made efforts to optimize the reaction conditions. As a result, they discovered surprisingly that the objective compound of acceptable quality could be obtained in good yield and have established a production-scale method for said neutralization. Thus, in accordance with the present invention, the reaction mixture is added dropwise to a cooled aqueous solution of an inorganic or organic base to neutralize the alkanesulfonic acid at a sustained low temperature. In this mode of operation, isomerization of constituent amino acid residues of the objective peptide can be successfully inhibited and the objective compound be obtained either as solid or as oil.

The inorganic base that can be used for this purpose includes sodium hydroxide, potassium hydroxide, calcium hydroxide, sodium carbonate, potassium carbonate, calcium carbonate, etc., and the organic base that can be used includes pyridine, triethylamine, etc., although potassium carbonate is particularly advantageous. When a carbonate is used as said base, copious foaming due to evolution of carbon dioxide gas is inevitable but this foaming can be controlled by adding an organic solvent such as ethyl acetate or benzene in a suitable proportion beforehand. The amount of said inorganic or organic base need only be sufficient to neutralize the alkanesulfonic acid but is preferably about 1 to 1.3 equivalents relative to the alkanesulfonic acid.

In order that the isomerization of amino acid residues and hydrolytic cleavage of the peptide chain may be inhibited and freezing of said aqueous solution of inorganic or organic base may be prevented, the neutralization system temperature is preferably controlled at about −15 to 15° C., preferably about −5 to 5° C.

Upon neutralization, the objective compound usually separates out as solid or oil from the neutralization system and, therefore, can be recovered by a suitable known procedure such as filtration or decantation.

The objective compound separated from the neutralization system can be purified by per se known procedures. In the purification of a relatively small amount of the objective compound, liquid chromatography constitutes a method of choice. For the purification of a large amount of the objective compound, there can be employed a combination of several known column chromatographic systems according to the ionic nature, polarity and other solution properties, aromaticity, and molecular weight of the particular compound.

The fractional purification technology preferred from industrial points of view includes a judicious combination of column chromatographic systems using a hyperporous resin such as Amberlite XAD-2 (Rohm & Haas Co., USA) or Diaion HP-20 (Mitsubishi Chemical, Japan), carboxymethylcellulose (CMC, CM-23 (Whatman, USA)), an ion exchange resin such as Amberlite CG-50 (Rohm & Haas Co., USA), and a molecular sieve resin such as Sephadex LH-20 (Pharmacia Fine Chemicals, Sweden). This procedure is procedurally simple and safe and provides for good reproducibility of both yield and quality, besides being economical.

An exemplary combination of column chromatographic systems may be a serial combination of Diaion HP-20 (mentioned above) (lst run)—CM-23 (mentioned above)—Diaion HP-20 (2nd run) - Sephadex LH-20 (mentioned above). When a solution containing a peptide is subjected to concentration, it emerges vigorous foaming, and it is necessary to use a lyophilizing machine, or to add an antifoaming agent. However, the combination of said column chromatography brings an advantageous method that the concentration procedure is omitted, the concentration being that on the effective fraction obtained in each column chromatography, especially the concentration of a large amount of the aqueous solution containing the effective fraction obtained by column chromatography of CM-23. Therefore, the combination of the above chromatography provides an industrially advantageous method in terms of operability and economically, as well as high quality which depend upon restraining decomposition of peptides due to concentration.

Diaion HP-20 (1st run) column chromatography has for its primary object to eliminate inorganic contaminants, as well as the radical scavenger added in the deprotection step and its reaction product, the antioxidant optionally added, and isomers of the objective compound as produced in minor amounts, from the solid or oil containing the crude objective compound as separated from the reaction mixture after the deprotection reaction. Referring, further, to this Diaion HP-20 (lst run) column chromatography, Diaion HP-20 is used in a proportion of about 20 to 40 (v/w) times, preferably about 25 to 35 times, relative to the objective compound. Elution of the objective compound and contaminants is generally carried out with an aqueous solution of acetone, methanol, or ethanol. In the following exemplary description, ethanol is used. First, the aqueous solution containing the objective compound is run on a Diaion HP-20 column and the column is irrigated serially with programmed amounts of sodium acetate/water preadjusted to pH 5 to 7 with acetic acid, ammonium acetate/water, and 10% (v/v) ethanol to elute related compounds. Then, the objective compound is eluted with 15% (v/v) ethanol and 35% (v/v) ethanol and the programmed fractions are pooled.

CM-23 column chromatography has for its primary object to eliminate byproducts tonically non-equivalent to the objective compound, and CM-23 is used in a proportion of generally 35 to 60 times (vlw), preferably 40–55 times (v/w), relative to the objective compound. The solution available after distillation of ethanol from the programmed eluate from the Diaion HP-20 (1st run) column is run on a CM-23 column and the column is first rinsed with water. The objective compound is then eluted by serial elution with 0.015 M ammonium acetate/water and 0.03 M ammonium acetate/water and the programmed fractions are pooled.

Diaion HP-20 (2nd run) column chromatography has for its primary object to remove the ammonium acetate used in elution from the CM-23 column and concentrate the large amount of eluate. The programmed eluate available after CM-23 column chromatography (a large quantity of aqueous solution which would give copious foaming on concentration) can be applied directly, i.e. without prior concentration, to the Diaion HP-20 (2nd run) column. This Diaion HP-20 (2nd run) column is irrigated serially with sodium acetate/water preadjusted to pH about 5 to 7 with acetic acid, ammonium acetate/water, and water in the order mentioned. The objective compound is then eluted with 15% (v/v) ethanol and 35% (v/v) ethanol and the programmed fractions are pooled. The programmed eluate thus obtained from the Diaion HP-20 (2nd run) column (which has been concentrated to about ⅓ by volume of the programmed eluate from the CM-23 column) is concentrated under reduced pressure and the residue is run on a Sephadex LH-20 column.

Sephadex LH-20 column chromatography, which is the final stage of the cascade, has for its object to eliminate pyrogenic substances, inorganic matter, and other trace contaminants. Sephadex LH-20 is used in a proportion of about 20 to 60 times (v/w), preferably about 30 to 50 times (vi/w), relative to the objective compound. The LH-20 column is developed with 0.005N acetic acid/$H_2O$ and the programmed fractions are pooled. Where necessary, this programmed eluate is concentrated, treated with active charcoal, membrane-filtered, and lyophilized to give the objective compound (acetate) as a final product.

Thus obtained Peptide (I) has a LHRH agonist activity, and can be used, for example, a similar manner as described in U.S. Pat. No. 4,008,209.

EXAMPLES

The following examples are intended to describe the present invention merely in further detail and should by no means be construed as defining the scope of the invention.

Reference Example 1
Production of Z—Tyr—D—Leu—OEt

Z—TyrOH•DCHA (58.8 g) was desalted with 1N-sulfuric acid in about 300 ml of ethyl acetate at 0 to 10° C. The organic layer was separated and dehydrated over anhydrous sodium sulfate ($Na_2SO_4$). After the $Na_2SO_4$ was filtered off, 24.3 g of D—Leu—OEt, 12.6 g of triethylamine, and 26.8 g of DCC were added to the filtrate and the mixture was stirred at about 5° C. for about 2 hours and further at about 10° C. for 5 hours. To this reaction mixture was added 60 ml of 1 N-hydrochloric acid and the mixture was filtered. The filtrate was allowed to stand and the organic layer was washed with aqueous solution of NaCl and aqueous solution of $NaHCO_3$ and the ethyl acetate was distilled off. To the residue was added isopropyl ether and the resulting crystal crop was harvested by filtration, recrystallized from ethyl acetate-isopropyl ether, and dried.

Yield 41.6 g (77%)

m.p. 116–118° C.

Optical rotation $[\alpha]_D^{25} = -3.4°$ (c=1, DMF)

Reference Example 2
Production of Z—Ser—Tyr—D—Leu—OEt

In about 300 ml of DMF were dissolved 40.5 g of Z—Tyr—D—Leu—OEt and 16.9 g of p-toluenesulfonic acid monohydrate, and hydrogenation was carried out in the presence of about 5 g of 5% Pd—C at 20 to 35° C. After completion of the reaction, the catalyst was filtered off.

Separately, 23.3 g of Z—Ser—OH and 19.2 g of HONB were dissolved in 300 ml of DMF followed by addition of 22.1 g of DCC and the mixture was stirred at 0 to 5° C. for about 7 hours. To this mixture was added the above reduction reaction mixture. The mixture was cooled to about 0° C. and 9 g of triethylamine was added dropwise. The mixture was then stirred at –5 to 5° C. for about 10 hours and left standing at room temperature overnight.

The crystals which formed were filtered off and the filtrate was concentrated under reduced pressure. The residue was dissolved in ethyl acetate. This ethyl acetate solution was washed with 1 N—HCl, aqueous solution of NaCl, and aqueous solution of $NaHCO_3$ in that order, and dehydrated over $Na_2SO_4$. After the $Na_2SO_4$ was filtered off, the filtrate was concentrated under reduced pressure and diluted with isopropyl ether. The resulting crude crystal crop was harvested by filtration, recrystallized from ethyl acetate, and dried.

Yield 37.6 g (77%)

m.p. 134–136° C.

Optical rotation $[\alpha]_D^{25} = -4.8°$ (c=1, DMF)

Reference Example 3
Procution of Z—Trp—Ser—Tyr—D—Leu—OEt (SEQ ID NO: 7) (ETSTLE)

In 300 ml of DMF was dissolved 36.2 g of Z—Ser—Tyr—D—Leu—OEt, and hydrogenation was carried out in the presence of about 5 g of 5% Pd—C at 25 to 35° C. After completion of the reaction, the catalyst was filtered off.

Separately, 21.4 g of Z—Trp—OH and 11.9 g of HONB were dissolved in about 300 ml of DMF followed by addition of 13.7 g of DCC and the mixture was stirred at 5 to 10° C. for about 7 hours. To this mixture was added the above reduction reaction mixture. The mixture was then stirred at 10 to 15° C. for about 7 hours and left standing at room temperature overnight.

The crystals which formed were filtered off and the filtrate was concentrated under reduced pressure. The residue was dissolved in ethyl acetate and this solution was washed with 1 N—HCl, aqueous solution of NaCl, and aqueous solution of $NaHCO_3$ in that order, and dehydrated over $Na_2SO_4$. After the $Na_2SO_4$ was filtered off, the filtrate was concentrated under reduced pressure and isopropyl ether was added to the residue. The resulting crude crystal crop was harvested by filtration, recrystallized from ethyl acetate-isopropyl ether, and dried.

Yield 41.3 g (85%)

Optical rotation $[\alpha]_D^{25} = -10.0°$ (c=1, EtOH)

Reference Example 4
Production of Z-5—oxo—Pro—His—Trp—Ser—Tyr—D—Leu—OEt (SEQ ID NO: 8)

In about 350 ml of DMF was dissolved 55.7 g of Z—Trp—Ser—Tyr—D—Leu—OEt (ZTSTLE), and hydrogenation was carried out in the presence of about 12 g of 5% Pd—C (wet) at about 30° C. After completion of the reaction, the catalyst was filtered off. To the filtrate thus obtained were added 32.6 g of Z-5-oxo—Pro—His—OH•1.5 $H_7O$ and 27.4 g of HONB, and after cooling to 2 to 8° C., 20.5 g of DCC was added. The mixture was stirred at about 8° C. for about 60 hours.

This reaction mixture was further stirred at about 40° C. for about 2 hours and then filtered and the filtrate was concentrated under reduced pressure. To the residue was added about 1 L of ethyl acetate at about 60° C. and the mixture was stirred at 20 to 25° C. The resulting crude crystals were collected by filtration, suspended in DMF (ca 230 ml)-ethyl acetate (ca 530 ml), stirred, and recovered by filtration. The purified crystals (ZPGLE) thus obtained were not dried but directly submitted to the next reduction reaction.

Reference Example 5
Synthesis of 5-oxo—Pro—His—Trp—Ser—Tyr—D—Leu—OEt (SEQ ID NO: 9)

The ZPGLE obtained in Reference Example 4 was dissolved in about 900 ml of DMF and hydrogenation was carried out in the presence of 15 g of 5% Pd—C (wet) at about 30° C. After completion of the reaction, the catalyst was filtered off and the filtrate was concentrated to about 180 ml and subjected to the next hydrolysis reaction.

Reference Example 6
Production of Z—Leu—ONP

In 1.2 L of ethyl acetate was dissolved 125 g of Z—Leu—OH as well as 65.5 g of p-nitrophenol, followed by dropwise addition of a solution of 107 g of DCC in ethyl acetate at 0 to 5° C., and the mixture was stirred at 10 to 25° C. After completion of the reaction, crystals were filtered off and the filtrate was concentrated under reduced pressure. The residue was dissolved in ethanol and the crystals which formed were collected by filtration and dried in vacuo.

Yield 142 g (78%)
m.p. 92–94° C.
Optical rotation $[\alpha]_D^{25}=-42.5°$ (c=1, CH$_3$OH)

Reference Example 7
Production of Z—Arg(MBS)—Pro— NHC$_2$H$_5$

In 400 ml of ethyl acetate was suspended 34.1 g of Z—Arg(MBS)—OH—DCHA, followed by addition of 57 ml of 1 N-sulfuric acid at 0 to 10° C. The mixture was stirred and allowed to stand and the organic layer was washed with aqueous solution of sodium sulfate and concentrated under reduced pressure. On the other hand, 15.7 g of Z—Pro—NHC$_2$H$_5$ was dissolved in 30 ml of N,N-dimethylacetamide and hydrogenation was carried out in the presence of 2.3 g of 5% Pd—C. After completion of the reaction, the catalyst was filtered off. In the filtrate was dissolved the Z—Arg (MBS)—OH-containing concentration residue as well as 9.4 g of HONB. To this solution was added a solution of 12.8 g of DCC in N,N-dimethylacetamide dropwise and the mixture was stirred at 10 to 20° C. After completion of the reaction, the crystals which formed were filtered off and the filtrate was concentrated under reduced pressure. The residue was dissolved in 450 ml of ethyl acetate and washed serially with 1 N—HCl, aqueous solution of NaCl, and aqueous solution of NaHCO$_3$ in that order. The ethyl acetate was distilled off under reduced pressure and the residue was treated with ethyl acetate-ethanol. The resulting crude crystalline crop was recrystallized from ethanol and dried in vacuo.

Yield 22.4 g (72%)
Optical rotation $[\alpha]_D^{25}=-33.0°$ (c=1, CH$_3$OH)

Reference Example 8
Production of Z—Leu—Arg(MBS)—Pro —NHC$_2$H$_5$ (ZLAP)

In 160 ml of DMF were dissolved 20.3 g of Z—Arg (MBS)—Pro—NHC$_2$H$_5$ and 6.4 g of p-toluenesulfonic acid monohydrate, and hydrogenation was carried out in the presence of 2.3 g of 5% Pd—C. After completion of the reaction, the catalyst was filtered off and 3.4 g of triethylamine was added to the filtrate under ice-cooling. To this mixture was added 13.6 g of Z—Leu—ONP and the mixture was stirred at 10 to 15° C. After completion of the reaction, the reaction mixture was concentrated under reduced pressure and the residue was dissolved in 120 ml of ethyl acetate. This solution was washed serially with diluted hydrochloric acid, aqueous solution of NaHCO$_3$, and water. The ethyl acetate was then distilled off and the residue was applied to a silica gel column. The column was developed serially with ethyl acetate-isopropyl ether (1:1) and ethyl acetate-methanol (3:2) and the objective fractions were pooled and concentrated under reduced pressure. The residue was dissolved in ethyl acetate and treated with isopropyl ether and the resulting precipitate was recovered by filtration and dried in vacuo.

Yield 22.2 g (92%)
Optical rotation $[\alpha]_D^{25}=-39.0°$ (c=1, CH$_3$CH$_2$OH)

Example 1
Production of 5-oxo—Pro—His—Trp—Ser—Tyr—D—Leu—OH (SEQ ID NO: 10) (PGLOH)

To the concentrate obtained in Reference Example 5 was added a solution of 8.3 g of sodium hydroxide in 1 L of water dropwise at −3 to 0° C. and the mixture was stirred at about 0° C. for about 2 hours. After the completion of reaction was confirmed, the reaction mixture was neutralized by adding 210 ml of 1 N-hydrochloric acid dropwise at about 0° C. The crystals which formed were dissolved by heating and 1.5 g of active charcoal was added under heating. After stirring, the active charcoal was filtered off. The filtrate was allowed to cool and stirred at 15 to 25° C. for 35 hours. The resulting crystals were collected by filtration and dried in vacuo at about 60° C.

Yield 39.9 g (59.2%, based on ZTSTLE obtained in Reference Example 3)
Optical rotation $[\alpha]_D^{25}=-21.5°$ (c=0.5, DMF)

(1) Incidentally, whereas the objectionable isomerization at His in 2-position and Ser in 4-position after one hour of reaction using the above solvent system were 1.3% and 4.8%, respectively, at the reaction temperature of 20° C., the corresponding rates at the reaction temperature of 0° C. were 0.2% and 0.44%, respectively.

(2) While the crystallization procedure according to the present invention effectively eliminates various structurally related compounds, examples of this elimination effect are shown below with focus on the products of His-isomerization and Ser-isomerization which are the most significant related compounds.

TABLE 1

|  | Reaction mixture | Crystals |
|---|---|---|
| [D-His$^2$]compound | 0.88%* | 0.18% |
| [D-Ser$^4$]compound | 0.44% | 0.08% |

*Inclusive of the [D-His$^2$] isomer by-produced in the fragment condensation step of the method for the production of Peptide (e) from Peptide (c).

Example 2
Production of crystals of 5-oxo—Pro—His—Trp—Ser—Tyr—D—Leu—OH (SEQ ID NO: 10) (PGLOH)

To the concentrate obtained in Reference Example 5 was added a solution of 8.3 g of sodium hydroxide in 1 L of water dropwise at −3 to 0° C. and the mixture was stirred at about 0° C. for about 2 hours. After the completion of reaction was confirmed, the reaction mixture was neutralized by adding 210 ml of 1 N-hydrochloric acid dropwise at about 0° C. The crystals which formed were dissolved by heating and 1.5 g of active charcoal was added under heating. After stirring, the active charcoal was filtered off. The filtrate was allowed to aging at 18 to 22° C. for 80 hours. The resulting crystals were collected by filtration and dried in vacuo at about 60° C.

Yield 42.9 g (63.6%, based on ZTSTLE obtained in Reference Example 3)
Optical rotation $[\alpha]_D^{25}=-21.8°$ (c=0.5, DMF)

Example 3
Production of 5-oxo—Pro—His—Trp—Ser—Tyr—D—Leu—Leu—Arg(MBS)—Pro—NHC$_2$H$_5$ (SEQ ID NO: 11) (briefly, MBSTAP)

In 350 ml of DMF was dissolved 35.6 g of ZLAP, and hydrogenation was carried out in the presence of 7.3 g of 5% Pd—C. Upon completion of the reaction, the catalyst was filtered off and 36.9 g of PGLOH and 16.2 g of HONB were dissolved in the filtrate, followed by dropwise addition of a solution of 14 g of DCC in DMF at −4 to 8° C. The mixture was stirred at about 8° C. for 15 hours and further at about 20° C. for about 30 hours. After completion of the reaction, the resulting crystals were filtered off and the filtrate was concentrated under reduced pressure and dissolved in about 200 ml of ethanol. Then, about 2.3 L of ethyl acetate was added and the resulting crystalline solid was recovered by filtration. This crude product was dissolved in about 220 ml of ethanol and about 900 ml of ethyl acetate was added. The resulting solid was recovered by filtration and washed with dichloromethane to provide MBSTAP as a wet product. This wet product was not dried but directly submitted to the next reaction for elimination of MBS. Assay by HPLC revealed that the yield of MBSTAP was 51.1 g (82%).

Example 4
Production of 5-oxo—Pro—His—Trp—Ser—Tyr—D—Leu—Leu—Arg—Pro—NHC$_2$H$_5$·CH$_3$COOOH (SEQ ID NO:12) (briefly, TAP-144)
(1) Elimination of MBS In 800 g of methanesulfonic acid was dissolved 60 g of phenol, and the wet MBSTAP (equivalent to 51.1 g of MBSTAP) obtained in Example 1 was added to the solution under cooling. The mixture was then stirred at about 10° C. for 5 hours.

Separately, 690 g of potassium carbonate was dissolved in 2 L of water and mixed with about 400 ml of ethyl acetate. This mixture was cooled to −2 to 0° C. to provide an alkali solution. To this alkali solution was added the above de-MBS reaction mixture dropwise at about 0° C. After completion of dropwise addition, the mixture was allowed to stand and a buffer solution (pH 4) (a mixture of ca 3 L of 0.1-N sodium acetate and ca. 58 ml of acetic acid) was added to the upper layer (oil-ethyl acetate layer) to dissolve the oil. The mixture was then allowed to stand and the aqueous layer was washed with ethyl acetate.

The washed aqueous layer was adjusted to pH about 6 with 20% (w/w) solution of potassium carbonate and the oil that had separated out was removed to provide an aqueous solution of TAP-144.
(2) Purification of crude TAP-144

The above aqueous solution of TAP-144 was applied to a column (ca. 1.2 L) of DIAION™ HP-20. The column was then washed serially with about 2.5 L of 0.3 M sodium acetate/water (adjusted to pH 6.2 with acetic acid), about 3 L of 0.025 M ammonium acetate/water, and 4.3 L of 10% ethanol. Thereafter, 9.5 L of 15% ethanol and 9.5 L of 35% ethanol were passed in that order and the objective fractions were pooled and concentrated under reduced pressure to remove the ethanol (S1-TAP).

This S1-TAP was applied to a column (ca. 1.7 L) of CM™-23 and after the column was washed with 2 L of water, the objective compound was eluted serially with 15 L of 0.015 M ammonium acetate/water and 15 L of 0.03 M ammonium acetate/water and the objective fractions were pooled (S2-TAP).

The S2-TAP obtained above was applied to a column of DIAION™ HP-20 (ca. 0.7 L) and after the column was washed serially with about 2.1 L of 0.3 M sodium acetate (adjusted to pH 6.2 with acetic acid), 3.2 L of 0.01 M ammonium acetate/water, and 0.7 L of water, elution was carried out with 4.3 L of 15% ethanol and 5.4 L of 35% ethanol in that order. The objective fractions were pooled and concentrated under reduced pressure to about 200 ml. The residue was applied to a column of Sephadex LH-20 (ca. 10 L) and elution was carried out with 0.005N-acetic acid/H$_2$O. The objective fractions were pooled and subjected to treatment with active charcoal, ultrafiltration, concentration, and lyophilization to provide 31.8 g (67.6%) of TAP-144.

Content: 99.8% (HPLC, internal standard)
Optical rotation $[\alpha]_D^{20}$=−39.0° (c=1, 1% acetic acid)
Absorbance: 57 (281 nm), 55 (289 nm)

The process of the present invention has many advantages: namely i) the isomerization of His$^2$ and Ser$^4$ in the hydrolysis step is minimized, ii) the Peptide (II) can be obtained as quality crystals and the isomers by-produced in condensation and hydrolysis can be successfully removed, iii) the product compound available upon elimination of the alkoxybenzenesulfonyl group after treatment with an alkanesulfonic acid can be separated on a commercial scale, iv) the final compound can be purified on a commercial scale, v) the intermediate Peptide (b) can be obtained in good yield with the formation of byproducts being controlled, vi) the drying of intermediates Peptide (e) and Peptide (I') and the isolation of intermediate Peptide (IV) can be omitted. Thus, there is provided an industrial method for producing a peptide having LHRH agonistic activity.

We claim:

1. A method of producing a peptide (I) consisting of the amino acid sequence of SEQ ID No: 6 or its salts, which method comprises reacting a peptide (II) consisting of the amino acid sequence of SEQ ID No: 4 or its salts, with a peptide (III) consisting of the amino acid sequence of SEQ ID No: 15 or its salts to produce a peptide (I') consisting of the amino acid sequence of SEQ ID No: 5 or its salts, followed by subjecting the peptide (I') to a de-protecting group reaction using an acid to obtain the peptide (I), said acid being $C_{1-6}$ alkanesulfonic acid and being used at a ratio of about 5 to about 25 times (weight) of the peptide (I'), and followed by neutralizing the acid with a base at a temperature of about 15° C. to about −15° C.

2. The method according to claim 1, wherein (a) amino acid residue 2 of SEQ ID Nos: 4, 5 and 6 is His, (b) amino acid residue 5 of SEQ ID Nos: 4, 5 and 6 is Tyr, (c) amino acid residue 6 of SEQ ID Nos: 4, 5 and 6 is Gly, D—Leu, D—Trp, D—Val which may be substituted with $C_{1-4}$ alkyl, D—Ser, D—Ala which may be substituted with $C_{1-4}$ alkoxy, with naphthyl or with 2-methylindolyl, or D—His which may be substituted with $C_{7-10}$ aralkyl, (d) amino acid residue 7 of SEQ ID Nos: 5 and 6, and amino acid residue I of SEQ ID No: 15 is Leu, (e) amino acid residue 8 of SEQ ID No: 5, and amino acid residue 2 of SEQ ID No: 15 is Arg which is protected with a group selected from the group consisting of a $C_{1-6}$ alkoxybenzenesulfonyl group, a tri-$C_{1-6}$ alkylbenzenesulfonyl group and a nitro group, and (f) amino acid residue 9 of SEQ ID Nos: 5 and 6, and amino acid residue 3 of SEQ ID No: 15 is group, Pro—NH—R", wherein R" represents a hydrogen atom or an alkyl group which may optionally be substituted with hydroxyl.

3. The method according to claim 1, wherein (a) amino acid residue 2 of SEQ ID Nos: 4, 5 and 6 is His, (b) amino acid residue 5 of SEQ ID Nos: 4, 5 and 6 is Tyr, (c) amino acid residue 6 of SEQ ID Nos: 4, 5 and 6 is D—Leu, (d) amino acid residue 7 of SEQ ID Nos: 5 and 6, and amino acid residue 1 of SEQ ID No: 15 is Leu, (e) amino acid residue 8 of SEQ ID No: 5, and amino acid residue 2 of SEQ ID No: 15 is Arg which is protected with a $C_{1-6}$ alkoxybenzenesulfonyl group, and (f) amino acid residue 9 of SEQ ID Nos: 5 and 6, and amino acid residue 3 of SEQ ID No: 15 is group, Pro—NH—R", wherein R" represents a $C_{1-3}$ alkyl group which may optionally be substituted with hydroxyl.

4. The method according to claim 1, wherein the reaction of the peptide (II) or its salts with the peptide (III) or its salts is carried out at a temperature ranging from about 0° C. to about 40° C. for about 30 to about 60 hours.

5. A method of recovering and purifying a peptide (I) consisting of the amino acid sequence of SEQ ID No: 6 or its salts, which method comprises:

subjecting a peptide (I') consisting of the amino acid sequence of SEQ ID No: 5 or its salts to a de-protecting group reaction in the presence of an acid to obtain peptide (I), said acid being $C_{1-6}$ alkanesulfonic acid, neutralizing the acid with a base, and purifying by column chromatography peptide (I) to recover the peptide (I).

6. A crystal of a peptide (II) consisting of the amono acid sequence of SEQ ID NO: 4, or its salt.

7. A method of producing a crystal of a peptide (II) consisting of the amino acid sequence of SEQ ID NO: 4, or its salt, which method comprises cooling a solution containing peptide (II) to form a peptide (II) crystal.

8. The method according to claim 7, further comprising adding seed crystals during cooling to facilitate cystalization.

9. The method according to claim 7, wherein the solution of the peptide (II) or its salt is subjected to aging.

10. The method according to claim 9, wherein the solution of the peptide (II) or its salt with a concentration of about 0.01 to about 0.05 mole/liter is subjected to aging at a temperature ranging from about 10° C. to about 70° C. for about 10 to about 70 hours.

* * * * *

SEQUENCE LISTING

```
<160> NUMBER OF SEQ ID NOS:  15

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = Z-Trp
<221> NAME/KEY: Residue
<222> LOCATION: (3)
<223> OTHER INFORMATION: Xaa = Tyr or Phe
<221> NAME/KEY: Residue
<222> LOCATION: (4)
<223> OTHER INFORMATION: Xaa = optionally substituted Gly-OR (R=a
      protecting group) or optionally substituted alpha-D-amino acid
      residue-OR (R=a protecting group)

<400> SEQUENCE: 1

Xaa Ser Xaa Xaa
```

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = Z-5-oxo-Pro
<221> NAME/KEY: Residue
<222> LOCATION: (2)
<223> OTHER INFORMATION: Xaa = His, Tyr, Trp or p-NH2-Phe
<221> NAME/KEY: Residue
<222> LOCATION: (5)
<223> OTHER INFORMATION: Xaa = Tyr or Phe
<221> NAME/KEY: Residue
<222> LOCATION: (6)
<223> OTHER INFORMATION: Xaa = optionally substituted Gly-OR (R=a
      protective group) or optionally substituted alpha-D-amino acid
      residue-OR (R=a protective group)

<400> SEQUENCE: 2

Xaa Xaa Trp Ser Xaa Xaa
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (2)
<223> OTHER INFORMATION: Xaa = His, Tyr, Trp or p-NH2-Phe
<221> NAME/KEY: Residue
<222> LOCATION: (5)
<223> OTHER INFORMATION: Xaa = Tyr or Phe
<221> NAME/KEY: Residue
<222> LOCATION: (6)
<223> OTHER INFORMATION: Xaa=optionally substituted Gly-OR (R=a
      protective group) or optionally substituted alpha-D-amino acid
      residue-OR (R=a protective group)

<400> SEQUENCE: 3

Xaa Xaa Trp Ser Xaa Xaa
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (2)
<223> OTHER INFORMATION: Xaa = His, Tyr, Trp or p-NH2-Phe
<221> NAME/KEY: Residue
<222> LOCATION: (5)
<223> OTHER INFORMATION: Xaa = Tyr or Phe
<221> NAME/KEY: Residue
<222> LOCATION: (6)
<223> OTHER INFORMATION: Xaa = optionally substituted Gly or optionally
      substituted alpha-D-amino acid residue

<400> SEQUENCE: 4

```
Xaa Xaa Trp Ser Xaa Xaa
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (2)
<223> OTHER INFORMATION: Xaa = His, Tyr, Trp or p-NH2-Phe
<221> NAME/KEY: Residue
<222> LOCATION: (5)
<223> OTHER INFORMATION: Xaa = Tyr or Phe
<221> NAME/KEY: Residue
<222> LOCATION: (6)
<223> OTHER INFORMATION: Xaa = optionally substituted Gly or optionally
      substituted alpha-D-amino acid residue
<221> NAME/KEY: Residue
<222> LOCATION: (7)
<223> OTHER INFORMATION: Xaa = Leu, Ile, Nle
<221> NAME/KEY: Residue
<222> LOCATION: (8)
<223> OTHER INFORMATION: Xaa = Arg which has been protected
<221> NAME/KEY: Residue
<222> LOCATION: (9)
<223> OTHER INFORMATION: Xaa = Pro-R (R = (1) Gly-NH-R', wherein R'
      represents a hydrogen atom or an alkyl group which may optionally
      be substituted with a hydroxyl group or (2) NH-R", wherein R"
      represents a hydrogen atom, an alkyl group which may optionally be
      substituted with a hydroxyl group or an ureido group (-NH-CO-NH2))

<400> SEQUENCE: 5

Xaa Xaa Trp Ser Xaa Xaa Xaa Xaa Xaa
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (2)
<223> OTHER INFORMATION: Xaa = His, Tyr, Trp or p-NH2-Phe
<221> NAME/KEY: Residue
<222> LOCATION: (5)
<223> OTHER INFORMATION: Xaa = Tyr or Phe
<221> NAME/KEY: Residue
<222> LOCATION: (6)
<223> OTHER INFORMATION: Xaa = optionally substituted Gly or optionally
      substituted alpha-D-amino acid residue
<221> NAME/KEY: Residue
<222> LOCATION: (7)
<223> OTHER INFORMATION: Xaa = Leu, Ile, Nle
<221> NAME/KEY: Residue
<222> LOCATION: (9)
<223> OTHER INFORMATION: Xaa = Pro-R (R= (1) Gly-NH-R', wherein R'
      represents a hydrogen atom or an alkyl group which may optionally
      be substituted with a hydroxyl group or (2) NH-R", wherein R"
      represents a hydrogen atom, an alkyl group which may optionally be
      substituted with a hydroxyl group or an ureido group (-NH-CO-NH2))

<400> SEQUENCE: 6

Xaa Xaa Trp Ser Xaa Xaa Xaa Arg Xaa
 1               5
```

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = Z-Trp
<221> NAME/KEY: Residue
<222> LOCATION: (4)
<223> OTHER INFORMATION: Xaa = D-Leu-O-C2H5

<400> SEQUENCE: 7

Xaa Ser Tyr Xaa
  1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = Z-5-oxo-Pro
<221> NAME/KEY: Residue
<222> LOCATION: (6)
<223> OTHER INFORMATION: Xaa = D-Leu-O-C2H5

<400> SEQUENCE: 8

Xaa His Trp Ser Tyr Xaa
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (6)
<223> OTHER INFORMATION: Xaa = D-Leu-O-C2H5

<400> SEQUENCE: 9

Xaa His Trp Ser Tyr Xaa
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (6)
<223> OTHER INFORMATION: Xaa = D-Leu

<400> SEQUENCE: 10

Xaa His Trp Ser Tyr Xaa
  1               5

<210> SEQ ID NO 11
<211> LENGTH: 9
<212> TYPE: PRT
```

```
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (6)
<223> OTHER INFORMATION: Xaa = D-Leu
<221> NAME/KEY: Residue
<222> LOCATION: (8)
<223> OTHER INFORMATION: Xaa = Arg which has been protected by
      p-methoxybenzenesulfonyl
<221> NAME/KEY: Residue
<222> LOCATION: (9)
<223> OTHER INFORMATION: Xaa = Pro-NH-C2H5

<400> SEQUENCE: 11

Xaa His Trp Ser Tyr Xaa Leu Xaa Xaa
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = 5-oxo-Pro
<221> NAME/KEY: Residue
<222> LOCATION: (6)
<223> OTHER INFORMATION: Xaa = D-Leu
<221> NAME/KEY: Residue
<222> LOCATION: (9)
<223> OTHER INFORMATION: Xaa = Pro-NH-C2H5

<400> SEQUENCE: 12

Xaa His Trp Ser Tyr Xaa Leu Arg Xaa
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Peptide
<221> NAME/KEY: Residue
<222> LOCATION: (1)
<223> OTHER INFORMATION: Xaa = (Pyr)Glu
<221> NAME/KEY: Residue
<222> LOCATION: (5)
<223> OTHER INFORMATION: Xaa = Tyr or Phe
<221> NAME/KEY: Residue
<222> LOCATION: (6)
<223> OTHER INFORMATION: Xaa = D-Leu, D-NLe, D-NVa, D-Ser, D-Abu,
      D-Phg, D-Phe or alpha-Aibu
<221> NAME/KEY: Residue
<222> LOCATION: (7)
<223> OTHER INFORMATION: Xaa = Leu, Ile or Nle
<221> NAME/KEY: Residue
<222> LOCATION: (9)
<223> OTHER INFORMATION: Xaa = Pro-NH-R, wherein R represents an alkyl
      group which may optionally have hydroxyl.

<400> SEQUENCE: 13

Xaa His Trp Ser Xaa Xaa Xaa Arg Xaa
 1               5

<210> SEQ ID NO 14
<211> LENGTH: 9
<212> TYPE: PRT
<213> ORGANISM: Artificial Sequence
```

```
-continued

<220> FEATURE:
<223> OTHER INFORMATION: Description of Artificial Sequence: Peptide
<221> NAME/KEY: Residue
<222> LOCATION: (1)
<223> OTHER INFORMATION: Xaa = (Pyr)Glu
<221> NAME/KEY: Residue
<222> LOCATION: (6)
<223> OTHER INFORMATION: Xaa = D-Leu
<221> NAME/KEY: Residue
<222> LOCATION: (8)
<223> OTHER INFORMATION: Xaa = Arg(p-methoxybenzenesulfonyl group)
<221> NAME/KEY: Residue
<222> LOCATION: (9)
<223> OTHER INFORMATION: Xaa = PRO-NH-C2H5

<400> SEQUENCE: 14

Xaa His Trp Ser Tyr Xaa Leu Xaa Xaa
 1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence:  Peptide
<221> NAME/KEY: Residue
<222> LOCATION: (1)
<223> OTHER INFORMATION: Xaa = H-Leu, H-Ile or H-Nle
<221> NAME/KEY: Residue
<222> LOCATION: (2)
<223> OTHER INFORMATION: Xaa = Arg which has been protected
<221> NAME/KEY: Residue
<222> LOCATION: (3)
<223> OTHER INFORMATION: Xaa = Pro-R (R = (1) Gly-NH-R', wherein R'
     represents a hydrogen atom or an alkyl group which may optionally
     substituted with a hydroxyl group or (2) NH-R", wherein R"
     represents a hydrogen atom, an alkyl group which may optionally be
     substituted with a hydroxyl group or an oreido group (-NH-CO-NH2))

<400> SEQUENCE: 15

Xaa Xaa Xaa
```